Oct. 11, 1932. P. M. PIERSON Plant Pat. 33
HYBRID TEA ROSE
Filed Jan. 23, 1932
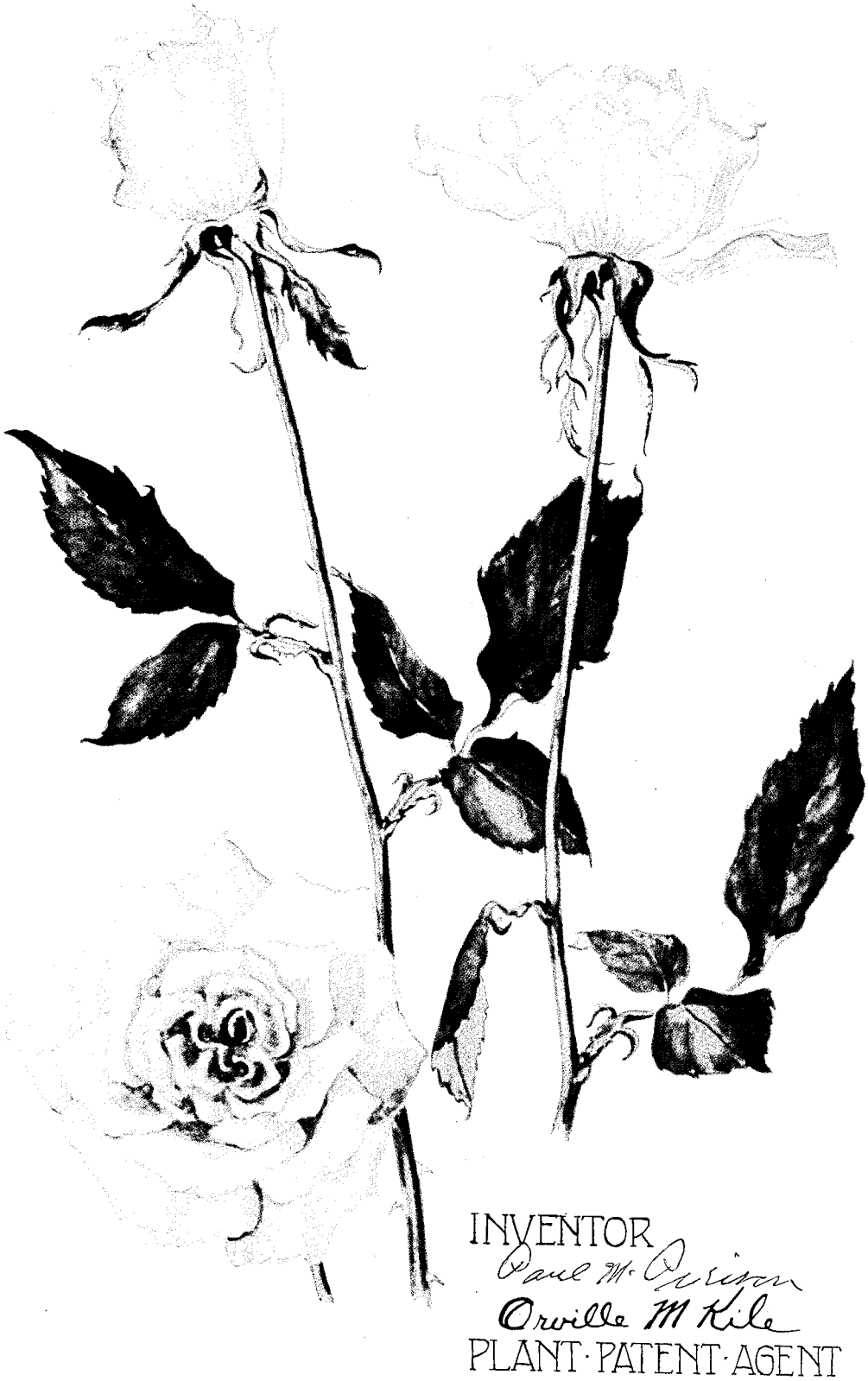

Patented Oct. 11, 1932

Plant Pat. 33

UNITED STATES PATENT OFFICE

PAUL M. PIERSON, OF OSSINING, NEW YORK

HYBRID TEA ROSE

Application filed January 23, 1932. Serial No. 588,460.

My invention relates to improvements in fragrant hybrid tea roses. The object of my invention is to provide a new and distinct variety of rose of the type mentioned, having desirable and pleasing combinations of qualities not previously existing in any known single variety. More specifically stated, my invention consists in the production of a new and distinct variety of rose having all the desirable qualities of the well known variety known and distinguished by the name Briarcliff, also originated by myself, and in addition possessing a distinctive and much more desirable and valuable color.

The feature of my new rose which distinguishes it at a glance from Briarcliff, is its depth and brilliance of color.

This new variety is a sport or mutation of Briarcliff. I first observed it in one of my greenhouses at Briarcliff Manor, New York, in the early winter of 1929. I make it a part of my business to search frequently among the thousands of roses grown by me to discover as early as possible any sport which seems to have superior qualities. I then test these sports or mutants in special trial beds to make certain that the apparently new qualities are inherent and not the result of some external factor. The promising mutants are then developed and reproduced and the others destroyed. By this means this new variety has been brought to a state of perfection and the stock increased and tested on a commercial scale. The first cut blossoms were offered for sale in September, 1931. None of the plants have yet been offered for sale.

The accompanying illustrations show in full natural color the blossom partly opened—at approximately the cutting stage—a more fully opened flower, and finally the full blown flower. These roses had been cut and packed in an approximately air tight, iced package for 24 to 30 hours at the time the paintings were made.

The following is a detailed description of this rose:

A bush or upright rose, of medium height, vigorous growth and free blooming habit.

*Stems.*—Rather stoutish and sufficiently strong to hold the flower in an upright position, green, smooth, carrying relatively few thorns of a greenish color, straight and pointing downward at a rather sharp angle. The peduncle bearing the flower is nearly straight rather than zig-zag.

*Foliage.*—Bright green, petioles practically free of hairs. Stipules, wide and highly developed, particularly on the first leaf branch below the blossom, at which point the stipules develop large laterally curved tips forming in many cases a complete circle and constituting a characteristic of the variety. Leaves have toothed edges. First leaf below the blossom has a decided tendency toward irregularity of form including deep cuts, three-pointed effects, and small supplementary leaves.

*Hips.*—Only moderately tapered.

*Buds.*—Medium length with tendency toward irregularity of form before opening.

*Sepals.*—Five in number 1½ to 2 inches in length on the fully opened flower, one to three of the sepals developing into a leaflike, lanceolate appendage with coarsely toothed margins.

*Blossoms.*—Double. In the cutting stage measure about 2 inches across the top and open out later to a 4 inch spread, thus being of medium to large size.

*Petals.*—Regularly arranged, except in the center of the flower, broadly obovate in shape, rather thick and heavy. They number 38 to 40, including 3 to 5 rudimentary petals, in the month of October. When approaching full bloom under certain conditions the central 15 to 17 petals often arrange themselves around what appear to be two or three distinct centers as shown in the illustration. When closely examined, however, these are seen to be not actually multiple centers but groups of 5 to 8 of the central petals that have been curled or rolled so tightly as to hang together in separate groups even when the surrounding petals have opened widely. Later in the season—December—an examination of many blossoms of this variety showed them all to have single pointed centers.

The color which is the chief distinguishing characteristic of this variety is as follows, the terms used being strictly in accord with those used in Ridgeway's Color Standards and Nomenclature, edition of 1912. Looking down into the half-opened flower, the color is rose, the portion of the petals near the outer edge being almost rose red, whereas the color of the somewhat similar variety, Briarcliff, is deep rose pink fading out to rose pink. This distinctive color effect is intensified when the blossom is viewed from the side or from below, this being the position from which the blossom would be viewed when lying in the florist's box. While the color effect is rose as a whole, each petal has a lighter color near the central portion than at its outer edges. The yellowish color at the base of the petals is more limited in area and not given to suffusion upward on the petals as is the case in the Briarcliff variety. In fact, the yellow at the base of the petals of this new variety is scarcely visible unless the petals are pulled down and widely separated. The brilliance and depth of color of this new variety as compared with Briarcliff is quickly and vividly noted by florists and prospective purchasers who instinctively select the brighter color.

*Stamens.*—Rather large and numerous with large anthers, not visible except when the flowers are pulled apart.

Briefly stated, my new variety is almost if not entirely identical with Briarcliff, except as to its color which at all seasons and under all ordinary conditions of temperature, moisture and other growth factors, is very plainly and notably deeper and more brilliant than Briarcliff and therefore decidedly more useful and valuable.

I claim:

A hybrid tea rose substantially as shown and described, characterized particularly by its rose to rose red color as distinguished from the rose pink to deep rose pink color of the somewhat similar variety known as Briarcliff.

PAUL M. PIERSON.